United States Patent
Shehadeh (12)

(10) Patent No.: US 6,399,090 B1
(45) Date of Patent: Jun. 4, 2002

(54) INSULIN SUPPLEMENTED INFANT FORMULA

(75) Inventor: Naim Shehadeh, Kfar Yasif (IL)

(73) Assignee: Insotech Ltd., Kibbutzhaabarot (IL)

( * ) Notice: Subject to any disclaimer, the term of this patent is extended or adjusted under 35 U.S.C. 154(b) by 0 days.

(21) Appl. No.: 10/015,782

(22) Filed: Dec. 17, 2001

Related U.S. Application Data

(63) Continuation-in-part of application No. 09/701,652, filed as application No. PCT/US99/12594 on Jun. 3, 1999, which is a continuation of application No. 09/090,909, filed on Jun. 5, 1998, now abandoned.

(51) Int. Cl.$^7$ .............................. A61P 3/10; A61K 38/28
(52) U.S. Cl. ........................... 424/439; 514/3; 514/866; 424/439
(58) Field of Search ...................... 514/3, 866; 424/439

(56) References Cited

U.S. PATENT DOCUMENTS 4,944,944 A * 7/1990 Tang et al. ................. 424/535

OTHER PUBLICATIONS

Wold et al. Defense factors in human milk, Current Opinion in Gastroenterology, 1994, vol. 6, pp. 652–658.*

* cited by examiner

*Primary Examiner*—Edward J. Webman
*Assistant Examiner*—Helen Nguyen
(74) *Attorney, Agent, or Firm*—Mark M. Friedman

(57) ABSTRACT

An infant formula in a powder or solution form including nutritional components and an insulin supplement. A method of feeding an infant including the steps of dissolving an infant formula powder containing nutritional components and an insulin supplement in water for obtaining a solution including said nutritional components and said insulin supplement and feeding the infant with the solution.

24 Claims, No Drawings

INSULIN SUPPLEMENTED INFANT FORMULA

This application is a continuation in part of U.S. patent application Ser. No. 09/701,652 filed in Nov. 30$^{th}$, 2000, which is a 371 of PCT U.S. 99/12594 filed on Jun. 3, 1999, which is a continuation of U.S. Ser. No. 09/090,909, filed Jun. 5, 1998, now abandoned.

FIELD AND BACKGROUND OF THE INVENTION

The present invention relates to an infant formula and, more particularly, to an insulin supplemented infant formula.

Breastfeeding, the natural feeding mode, has multiple beneficial effects on the infant. First, it is known to be the most suitable diet for infant's nutritional requirements. Second, it provides the infant with immune protection against a wide range of infection related diseases (1). Third, as it contains active insulin molecules it protects the infant against the development of Type-1 diabetes (2–3). Fourth, insulin present in milk enhances small intestinal growth and development (4).

Type-1 diabetes, which is insulin dependent diabetes mellitus (IDDM), is the consequence of progressive autoimmune pancreatic β cell destruction during an initially asymptomatic period that may extend many years (5–6). The etiology is multifactorial, with genetic and environmental factors contributing to the autoimmune destruction of the β cells. The fact that concordance for IDDM in monozygotic twins is not more than 30–50% (7) and that 90% of patients with newly diagnosed IDDM do not have an affected first-degree relative having IDDM (8), as well as the sudden increase in incidence of IDDM witnessed over the last ten years (9), have been taken as indication of the importance of environmental factors in triggering the development of the autoimmune process in genetically susceptible individuals.

Many studies show that type I diabetes is related to cow's milk consumption and neonatal feeding practices (2,10). In the case-control studies (including a study conducted in the Juvenile Diabetes Unit of the Rambam Medical Center, Haifa, Israel), patients with type I diabetes were more likely to have been breast-fed for less than 3 months and to have been exposed to cow's milk proteins before 3 months of age (3). Moreover, the immune system of patients with IDDM recognizes cow's milk proteins, as demonstrated by antibodies assays and lymphocytes activity tests (11). These data emphasize the importance of diet and orally administered proteins on the development of autoimmune diabetes.

In animal models, It has been shown that oral feeding of a specific antigen can suppress the immune system and cause an antigen-specific reduction in many types of immune responses, including T cell proliferation; delayed type hypersensitivity, and antibody production (12–15). Oral administration of insulin generates active cellular mechanisms that suppress the development of autoimmune diabetes (16). These results have paved the way to the "oral tolerance approach" and oral insulin treatment is already taking place in human trials planned to prevent type 1 diabetes in high risk groups (17).

As shown below, prior art infant formulas, although attempting to mimic as much as possible breast milk, are very low in immunologically recognizable insulin as compared with human milk. The level of active insulin in these formulas is probably zero, due to the harsh conditions associated with their manufacture.

There is thus a widely recognized need for, and it would be highly advantageous to have, an infant formula supplemented with insulin.

SUMMARY OF THE INVENTION

According to one aspect of the present invention there is provided an infant formula in a powder or solution form comprising nutritional components and an insulin supplement such that when the infant formula is fed to an infant a chance of the infant of developing diabetes is reduced;

wherein said insulin is in a concentration range of about 1,000 to 100,000 micro units/100ml of solution or 8,300–750,000 micro units/100 grams of powder.

According to another aspect of the present invention there is provided a method of feeding an infant comprising the steps of dissolving an infant formula powder containing nutritional components and an insulin supplement in water for obtaining a solution including the nutritional components and the insulin supplement and feeding the infant with the solution thereby reducing a chance of the infant of developing diabetes;

wherein said insulin is in a concentration range of about 1,000 to 100,000 micro units/100ml of solution or 8,300–750,000 micro units/100 grams of powder.

According to further features in preferred embodiments of the invention described below, the insulin is recombinant insulin.

According to still further features in the described preferred embodiments the insulin is synthetic.

According to still further features in the described preferred embodiments the insulin is purified natural insulin.

According to still further features in the described preferred embodiments the insulin is biologically active.

According to still further features in the described preferred embodiments the insulin is in a concentration range of about 17,000 to 400,000 µU per 100 grams of said powder or 2,000–55,000 µU per 100 milliliters of said solution.

According to still further features in the described preferred embodiments the insulin has an amino acid sequence of human insulin.

According to still further features in the described preferred embodiments at least some of the nutritional components are derived from milk or soy.

The present invention successfully addresses the shortcomings of the presently known configurations by providing an infant formula which is more similar to human milk, protects from the development of Type-1 diabetes and improve the development and maturation of infants intestine.

DESCRIPTION OF THE PREFERRED EMBODIMENTS

The present invention is of an infant formula supplemented with insulin, preferably human insulin, which can be used to feed infants. Specifically, the present invention can be used to protect infants of syndromes associated with feed devoid of insulin fed to them in the first year of their lives. The present invention renders infant formulas more similar to human milk.

The principles and operation of an infant formula according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Epidemiological and experimental animal data suggest that insulin content in infant diet may play an important role in preventing autoimmune diabetes and improving intestinal development.

It is shown in the Examples section hereinunder that the level of immunologically recognized insulin in a variety of commonly used infant formulas is very low, at least four to ten times lower as compared with human milk, probably even lower. Although not tested, the level of active insulin in such formulas is expected to be zero due to the harsh conditions associated with their manufacture. Soy-based infant formulas, are devoid of milk content, and are therefore completely devoid of both immunologically recognizable insulin, not to mention active insulin.

Moreover, it has been shown that exposure to bovine insulin present in fresh cow milk, which differs from human insulin only by three amino acids, may break the tolerance to insulin and lead to autoimmune diabetes (18), To overcome these two obstacles in infant feeding: the lack of insulin in infant formulas and the risk to break immune tolerance to insulin when using fresh cow milk, it is herein suggest for the first time to add human insulin to infant formula.

Addition of insulin to infant formula leads for the following beneficial effects. First, it renders the infant formula more similar to human milk. Second, it protects from the development of Type-1 diabetes. Third, it improve the development and maturation of infants intestine. The addition of insulin to infant formula is safe for at least two reasons. First, the concentration of insulin is selected similar to that found in human milk. Second, oral insulin administration is already used in several human trials (17).

Thus, in accordance with one aspect of the present invention there is provided an infant formula in a powder or solution form which formula includes nutritional components and an insulin supplement.

In accordance with another aspect of the present invention there is provided a method of feeding an infant. The method is effected by executing the following steps. First an infant formula powder containing nutritional components and an insulin supplement is solubilized in water for obtaining a solution including the nutritional components and the insulin supplement. Second, the solution is fed to the infant.

As exemplified in the Examples section below, the nutritional components may include milk or soy derived nutritional components. They may additionally include one or more of the following ingredients: lactose, vegetable oils, skimmed milk powder, whey protein concentrate, Sodium, Calcium, Phosphorus, Potassium, Chloride, Iron, Magnesium, Taurine, Vitamins, Glucose syrup, soy protein isolate, Sucrose, Maltodextrine, Methionine, Taurine, Carnitine, and trace elements.

According to a preferred embodiment of the present invention, the insulin is selected from the following insulin types: recombinant insulin, synthetic insulin, purified natural insulin, biologically active insulin and insulin having an amino acid sequence of human insulin (e.g., human insulin). Some of these types are overlapping and therefore the insulin of choice may be categorized to more than a single type of the types listed. Human recombinant insulin is available in a pure form from Eli Lilly & Co, USA. Human natural purified insulin is available in a pure form from Novo Nordisk, Denmark. Crude extracts may also be useful, depending on the method of their manufacturing. Synthetic insulin may be manufactured using commercially available building units for Boc and Fmoc chemistry peptide synthesis, as well known in the art.

According to another preferred embodiment of the present invention the concentration of the insulin in the solution is similar to the concentration in human milk. Thus, according to a preferred embodiment the insulin concentration is in the range of about 25000–75000 µU per 100 grams of the powder (which is diluted about 7.5 fold to form the solution) or 3000–10000 µU per 100 milliliters of the solution, preferably 3000–6000, optimally about 4200 µU per 100 milliliters of the solution.

EXAMPLES

Reference is now made to the following examples, which together with the above descriptions, illustrate the invention in a non limiting fashion.

Materials and Methods
Milk Samples and Insulin Measurements

Human breast milk samples were collected from mothers between the second and the 30th day after delivery of full term pregnancies. Cow milk samples were taken from pooled fresh commercially available milk. Cow milk formulas were prepared according to manufacturer instructions. All samples were stored in polypropylene tubes at −20° C. Fat-free infranatant were obtained by diluting the milk samples with PBS (10 mM $KH_2PO_4$, 0.15 M NaCl, pH 7.4) and centrifuged at 100,000 g for 60 min. Clear infranatant were aspirated and stored at −20° C. Insulin concentrations were determined by radioimmunoassay with commercial kit (Bio Data, Sorin) using human insulin as standard.

Experimental Results

As shown in Table 1 below, insulin concentration is significantly higher in human milk (about 42 µU/ml) compared with commercial fresh cow milk (about 17 µU/ml) and infant formulas (about 4–12 µU/ml). Insulin levels in infant formulas is very low and is similar to the levels recorded for negative control solution (0.5% bovine serum albumin solution, about 6 µU/ml).

TABLE 1

Insulin concentration in milk samples

| Milk Sample | Insulin Concentration (mean in µU/ml) |
| --- | --- |
| Human milk, n = 29 | 42 |
| Fresh pooled cow milk, n = 4 (Tnuvah, Israel) | 17.08 |
| Materna Premium, n = 2 (Trima, Israel) | 7.5 |
| Remedia Formula, n = 3 (Humna Milchwerke ,Germany) | 7.0 |
| Similac, n = 2 (Ross-Abbott, Irland) | 11.85 |
| Enfalac Premature, n = 1 (Mead Johnson, USA) | 5.2 |
| Pregestimil, n = 2 (Mead Johnson, USA) | 3.8 |
| 0.5% Bovine Serum Albumin solution, n = 2 (Sigma, USA) | 6.5 |

Tables 2 and 3 below provide exemplary compositions of dry and in solution milk- and soy-bases infant formulas according to the present invention.

Infant Formula I (Milk-Based)

The formula comprises the following ingredients: lactose, vegetable oils, skimmed milk powder, whey protein concentrate, Sodium, Calcium, Phosphorus, Potassium, Chloride, Iron, Magnesium, Taurine, Vitamins and Insulin.

TABLE 2

|  | Unit | Powder 100 g | Solution 100 ml |
|---|---|---|---|
| General Comp. | | | |
| Protein | gram | 11.1 | 1.5 |
| Fat | gram | 25.9 | 3.5 |
| Lactose | gram | 55.5 | 7.5 |
| Water | gram | 2.5 | — |
| Ash | gram | 2.06 | 0.27 |
| Insulin | μU | 22500–75000 | 3000–10000 |
| Vitamins | | | |
| Vitamin A | I.U. | 1500 | 200 |
| Vitamin D | I.U. | 300 | 40 |
| Vitamin E | mg | 6 | 0.81 |
| Vitamin K | μg | 15 | 2.01 |
| Vitamin B1 | μg | 350 | 47.03 |
| Vitamin B2 | μg | 450 | 60 |
| Vitamin B6 | μg | 222 | 30 |
| Vitamin B12 | μg | 0.66 | 0.09 |
| Niacin | mg | 2 | 0.27 |
| Folic Acid | μg | 45 | 6 |
| Calcium Pantothenate | mg | 4.44 | 0.06 |
| Biotin | μg | 11 | 1.5 |
| Vitamin C | mg | 45 | 6.08 |
| Minerals | | | |
| Calcium | mg | 326 | 44 |
| Phosphorus | mg | 219 | 29.6 |
| Magnesium | mg | 37 | 5 |
| Iron | mg | 7.4 | 1 |
| Sodium | mg | 120.7 | 16.3 |
| Potassium | mg | 373 | 50 |
| Ca/p ratio | — | 1.49 | 1.49 |
| Amino Acid Profile | | | |
| Alanine | mg | 522 | 69.6 |
| Arginine | mg | 368 | 49.1 |
| Asparatic Acid | mg | 11.10 | 1.5 |
| Cystine | mg | 191 | 25.5 |
| Glutamic Acid | mg | 1423 | 189.7 |
| Glycine | mg | 244 | 32.5 |
| Histidine | mg | 262 | 34.9 |
| Isoleucine | mg | 761 | 101.5 |
| Leucine | mg | 12.20 | 1.62 |
| Lysine | mg | 10.00 | 1.3 |
| Methionine | mg | 270 | 36 |
| Phenylalanine | mg | 461 | 62.3 |
| Proline | mg | 962 | 128.3 |
| Serine | mg | 681 | 90.8 |
| Taurine | mg | 37 | 4.9 |
| Threonine | mg | 686 | 91.5 |
| Tryptophan | mg | 180 | 24 |
| Tyrosine | mg | 463 | 61.7 |
| Valine | mg | 775 | 103.3 |
| Fatty Acid Profile | | | |
| Caprylic (C8) | % from fat | 2.6 | 2.6 |
| Capric (C10) | % | 2.1 | 2.1 |
| Lauric (C12) | % | 17.5 | 17.5 |
| Meristic (C14) | % | 6.7 | 6.7 |
| Palmitic (C16) | % | 11.2 | 11.2 |
| Stearic (C18) | % | 11.8 | 11.8 |
| Oleic (C18:1) | % | 37.0 | 37.0 |
| Linoleic (C18:2) | % | 10.0 | 10.0 |
| Linolenic (C18:3) | % | 1.2 | 1.2 |
| Supplement | | | |
| Insulin | μU | 22500–75000 | 3000–10000 |

Infant Formula II (Soy-Based)

The formula comprises the following ingredients: Glucose syrup, vegetable oils, soy protein isolate, Sucrose, Maltodextrine, Sodium, Calcium, Phosphorus, Potassium, chloride, Iron, Magnesium, Vitamins, Methionine, Taurine, Carnitine, trace elements and Insulin.

TABLE 3

|  | Unit | Powder 100 g | Solution 100 ml |
|---|---|---|---|
| General Comp. | | | |
| Protein | gram | 15 | 1.98 |
| Fat | gram | 27.54 | 3.64 |
| Carbohydrate | gram | 51.5 | 6.8 |
| Linoleic Acid | gram | 4.5 | 0.6 |
| Insulin | μU | 22500–75000 | 3000–10000 |
| Vitamins | | | |
| Vitamin A | I.U. | 1500 | 198 |
| Vitamin D | I.U. | 300 | 39.7 |
| Vitamin E | I.U. | 10 | 1.32 |
| Vitamin C | mg | 65 | 8.6 |
| Vitamin K | μg | 77 | 10.2 |
| Vitamin B1 | μg | 345 | 45.6 |
| Vitamin B2 | μg | 445 | 58.9 |
| Vitamin B6 | μg | 327 | 43.3 |
| Vitamin B12 | μg | 1.5 | 0.2 |
| Niacin | mg | 7 | 0.93 |
| Folic Acid | μg | 76 | |
| Pantothenic Acid | μg | 4.5 | 0.6 |
| Biotin | μg | 25 | 3.3 |
| Choline | mg | 58 | 7.7 |
| Minerals | | | |
| Calcium | mg | 500 | 66.2 |
| Phosphorus | mg | 300 | 39.7 |
| Magnesium | mg | 45 | 6 |
| Iron | mg | 9.2 | 1.2 |
| Zinc | mg | 4 | 0.53 |
| Manganese | μg | 150 | 19.8 |
| Copper | μg | 400 | 53 |
| Iodine | μg | 77 | 10.2 |
| Sodium | mg | 200 | 26.5 |
| Potassium | mg | 546 | 72.2 |
| Chloride | mg | 400 | 53 |
| Inositol | mg | 25 | 3.3 |
| Carnitine | mg | 10 | 1.3 |
| Ca/P ratio | 1.67 | 1.67 | |
| Amino Acid Profile | | | |
| Alanine | mg | 640 | 85.3 |
| Arginine | mg | 497 | 6.5 |
| Aspartic Acid | mg | 1385 | 184.7 |
| Cystine | mg | 242 | 32.3 |
| Glutamic Acid | mg | 3065 | 408.7 |
| Glycine | mg | 300 | 40 |
| Histidine | mg | 382 | 50.9 |
| Isoleucine | mg | 893 | 119.1 |
| Leucine | mg | 1600 | 213.3 |
| Lysine | mg | 1360 | 181.3 |
| Methionine | mg | 406 | 54.1 |
| Phenylalanine | mg | 650 | 86.7 |
| Proline | mg | 1113 | 148.4 |
| Serine | mg | 737 | 98.3 |
| Taurine | mg | 51 | 6.8 |
| Threonine | mg | 460 | 61.3 |
| Tyrosine | mg | 621 | 82.8 |
| Valine | mg | 947 | 126.3 |
| Fatty Acid Profile | | | |
| Caprylic (C8) | % from fat | 2.6 | 2.6 |
| Capric (C10) | % | 2.1 | 2.1 |
| Lauric (C12) | % | 17.5 | 17.5 |
| Meristic (C14) | % | 6.7 | 6.7 |
| Palmitic (C16) | % | 11.2 | 11.2 |
| Stearic (C18) | % | 11.8 | 11.8 |
| Oleic (C18:1) | % | 37.0 | 37.0 |
| Linoleic (C18:2) | % | 10.0 | 10.0 |
| Linolenic (C18:3) | % | 1.2 | 1.2 |
| Supplement | | | |
| Insulin | μU | 22500–75000 | 3000–10000 |

Although the invention has been described in conjunction with specific embodiments thereof, it is evident that many

REFERENCES CITED

1. Wold A E, Hanson L A. Defense factors in human milk. Curr Opin Gastroenterol 10:652–8, 1994.
2. Kostraba J. What can epidemiology tell us about the role of infant diet in the etiology of IDDM?. Diabetes Care 17:87–91, 1994.
3. Verge C, Howard N, Irwig L, Simpson J, Mackerras D, Silink M. Environmental factors in childhood IDDM. Diabetes Care 17:1381–1388, 1994.
4. Shulman R J. Oral insulin increases small intestinal mass and disaccharidase activity in the newborn miniature pig. Pediatr Res 28:171–5, 1990.
5. Gorsuch A N, Spencer K N, Lister J, McNally J M, Bottazzo G F, Cudworth A G: Evidence for a long prediabetic period in type 1 (insulin-dependent) Diabetes. *Lancet* ii: 1363–1365, 1981.
6. Eisenbarth G: Autoimmune beta cell insufficiency: Diabetes mellitus type 1. *Triangle* 23:111–124, 1984.
7. Barnett A H, Eff C, Leslie R D G, Pyke D A. Diabetes in identical twins: a study of 200 pairs: *Diabetologia* 20:87–93, 1983.
8. LaPorte R E, Cruickshanks K J. Incidence and risk factors for insulin dependent diabetes. In: National Diabetes Data Group. Diabetes in America: diabetes data compiled 1984. Bethesda, Md.: Department of health and human services, III-1–III-12. (NIH publication no. 85–1468.), 1985.
9. Laron Z, Shamis I, Gordon O, Albaz Y: Increased incidence of childhood IDDM (0–17 yr) in Israel. *J Ped Endocrinol Met* 8:224, 1995.
10. Fava D, Leslie D, Pozzilli P. Relationship between dairy product consumption and incidence of IDDM in childhood in Italy. Diabetes Care 17:1488–1490, 1994.
11. Karjalainen J, Martin J M, Knip M, Ilonen J, Dosch H-M. A bovine albumin peptide as a possible trigger of insulin-dependent diabetes mellitus. N Engl J Med 327:302–307, 1992.
12. Weiner H L. Oral tolerance for the treatment of autoimmune diseases. Annu Rev Med 48:341–351, 1997.
13. Garside P, Mowat A M. Mechanisms of oral tolerance. Crit Rev Immunol 17:119, 1997.
14. Ke Y, Kapp J A. Oral antigen inhibits priming of CD8+ CTL, CD4+ T cells, and antibody responses while activating CD8+ suppressor T cells. J Immunol 156:916–21, 1996.
15. Bergerot I, Fabien N, Maguer V, Thivolet C. Oral administration of human insulin to NOD mice generates CD4+ T cells that suppress adoptive transfer of diabetes. J Autoimmun 7:65–71, 1994.
16. Zhang Z J, Davidson L, Eisenbarth G, Weiner H L. Suppression of diabetes in nonobese diabetic mice by oral administration of porcine insulin. Proc Natl Acad Sci USA 80:10252–10256, 1991.
17. Schatz D A, Rogers D G, Brouhard B H. Prevention of insulin-dependent diabetes mellitus: an overview of three trials. Cleve Clin J Med 63:270–4, 1996.
18. Vaarala O, Paronen J, Otonkoski T, Akerblom H K. Cow milk feeding induces antibodies to insulin in children—A link between cow milk and Insulin-Dependent Diabetes Mellitus?. Scand J Immunol 47:131–135, 1998.

What is claimed is:

1. An infant formula in a powder or solution form comprising nutritional components and an insulin supplement such that when the infant formula is fed to an infant a chance of the infant of developing diabetes is reduced; wherein said insulin is in a concentration range of about 1,000 to 100,000 micro units/100 ml of solution or 8,300–750,000 micro units/100 grams of powder.

2. The infant formula of claim 1, wherein said insulin has an amino acid sequence of human insulin.

3. The infant formula of claim 1, wherein said insulin is recombinant.

4. The infant formula of claim 3, wherein said insulin has an amino acid sequence of human insulin.

5. The infant formula of claim 1, wherein said insulin is synthetic.

6. The infant formula of claim 5, wherein said insulin has an amino acid sequence of human insulin.

7. The infant formula of claim 1, wherein said insulin is purified natural insulin.

8. The infant formula of claim 7, wherein said insulin has an amino acid sequence of human insulin.

9. The infant formula of claim 1, wherein said insulin is biologically active.

10. The infant formula of claim 1, wherein said insulin is in a concentration range of about 2,000 to 55,000 micro units/100 ml of solution or 17,000–400,000 micro units/100 grams of powder.

11. The infant formula of claim 1, wherein at least some of said nutritional components are derived from milk.

12. The infant formula of claim 1, wherein at least some of said nutritional components are derived from soy.

13. A method of feeding an infant comprising the steps of dissolving an infant formula powder containing nutritional components and an insulin supplement in water for obtaining a solution including said nutritional components and said insulin supplement and feeding the infant with said solution, thereby reducing a chance of the infant of developing diabetes; wherein said insulin is in a concentration range of about 1,000 to 100,000 micro units/100 ml of solution or 8,300–750,000 micro units/100 grams of powder.

14. The method of claim 13, wherein said insulin has an amino acid sequence of human insulin.

15. The method of claim 13, wherein said insulin is recombinant.

16. The method of claim 15, wherein said insulin has an amino acid sequence of human insulin.

17. The method of claim 13, wherein said insulin is synthetic.

18. The method of claim 17, wherein said insulin has an amino acid sequence of human insulin.

19. The method of claim 13, wherein said insulin is purified natural insulin.

20. The method of claim 19, wherein said insulin has an amino acid sequence of human insulin.

21. The method of claim 13, wherein said insulin is biologically active.

22. The method of claim 13, wherein said insulin is in a concentration range of about 17,000 to 400,000 $\mu$U per 100 grams of said powder or 2,000–55,000 $\mu$U per 100 milliliters of said solution.

23. The method of claim 13, wherein at least some of said nutritional components are derived from milk.

24. The method of claim 13, wherein at least some of said nutritional components are derived from soy.

* * * * *